United States Patent
Levinson et al.

(10) Patent No.: US 6,277,139 B1
(45) Date of Patent: Aug. 21, 2001

(54) VASCULAR PROTECTION AND EMBOLIC MATERIAL RETRIEVER

(75) Inventors: Melvin E. Levinson; George I. Golik, both of Miami, FL (US)

(73) Assignee: Scion Cardio-Vascular, Inc., Miami, FL (US)

(*) Notice: Subject to any disclaimer, the term of this patent is extended or adjusted under 35 U.S.C. 154(b) by 0 days.

(21) Appl. No.: 09/540,959

(22) Filed: Mar. 31, 2000

Related U.S. Application Data

(63) Continuation of application No. 09/376,120, filed on Aug. 17, 1999.
(60) Provisional application No. 60/127,438, filed on Apr. 1, 1999.

(51) Int. Cl.[7] .................................................. A61M 29/00
(52) U.S. Cl. ........................... 606/200; 606/159; 606/127
(58) Field of Search ................................ 606/110, 113, 606/114, 127, 159, 200, 167

(56) References Cited

U.S. PATENT DOCUMENTS

| | | |
|---|---|---|
| 4,619,246 | 10/1986 | Molgaard-Nielsen . |
| 4,723,549 | 2/1988 | Wholey et al. . |
| 5,053,008 | 10/1991 | Bajaj . |
| 5,108,419 | 4/1992 | Reger et al. ........................ 606/200 |
| 5,190,555 * | 3/1993 | Wetter et al. ...................... 606/114 |
| 5,192,286 * | 3/1993 | Phan et al. ........................ 606/127 |
| 5,549,626 | 8/1996 | Miller et al. ...................... 606/200 |
| 5,695,519 | 12/1997 | Summers et al. .................. 606/200 |
| 5,769,816 | 6/1998 | Barbut et al. ........................ 604/96 |
| 5,810,874 | 9/1998 | Lefebvre ............................ 606/200 |
| 5,814,064 | 9/1998 | Daniel et al. ...................... 606/200 |
| 5,911,734 | 6/1999 | Tsugita et al. ..................... 606/200 |
| 5,941,896 * | 8/1999 | Kerr ................................... 606/200 |
| 5,980,555 * | 11/1999 | Barbut et al. ...................... 606/200 |
| 6,001,118 * | 12/1999 | Daniel et al. ...................... 606/200 |
| 6,053,932 * | 4/2000 | Daniel et al. ...................... 606/200 |
| 6,059,814 * | 5/2000 | Ladd ................................... 606/200 |
| 6,171,327 * | 1/2001 | Daniel et al. ...................... 606/200 |

FOREIGN PATENT DOCUMENTS

WO96/01591  1/1996  (WO) .

\* cited by examiner

*Primary Examiner*—Glenn K. Dawson
(74) *Attorney, Agent, or Firm*—Robert C. Kain, Jr.; Fleit Kain

(57) ABSTRACT

The vascular protection and embolic material retrieval device is used in connection with a guidewire and a catheter sheath during catheter based procedures. The device includes a discontinuous loop of memory sheath material having an open loop shape when the loop is not radially restrained in the catheter sheath. When the loop is disposed beyond the distal end of the catheter sheath, the loop is deployed and forms a discontinuous loop due to the memory characteristic of the loop material. The device includes a lead line having a proximal end attached to the guidewire and a distal end attached to the discontinuous loop. A substantially conical filter adapted to capture embolic material has an open conical end attached to the discontinuous loop and a conical end point attached to the guidewire. When the loop is disposed outboard of the catheter sheath, the filter unfurls forming a conical filter trap for embolic material. In order to collapse the filter, the guidewire is pulled such that the lead line, loop and conical filter moves inboard towards the sheath's distal end and the filter collapses about any embolic material trap therein.

22 Claims, 10 Drawing Sheets

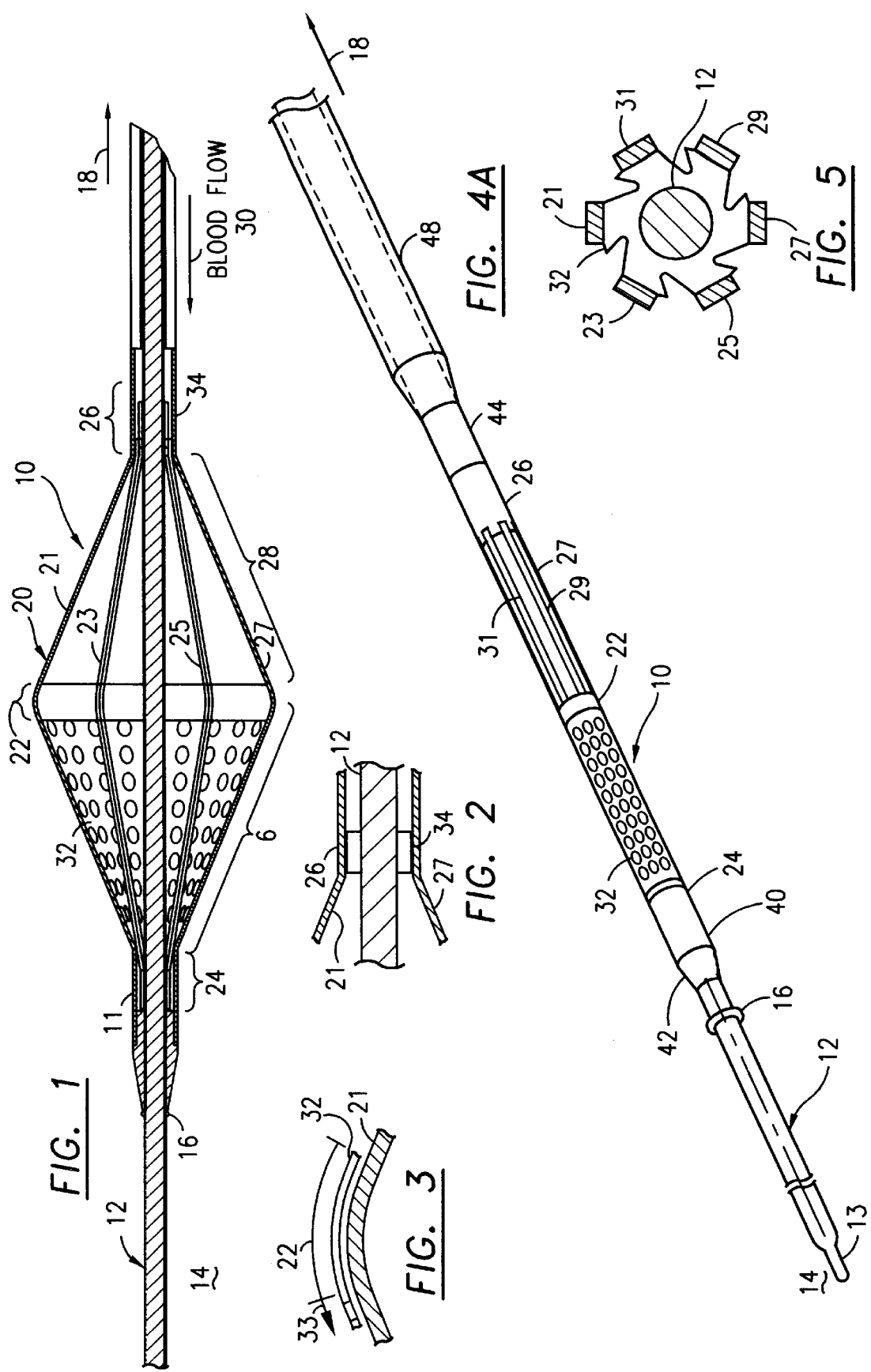

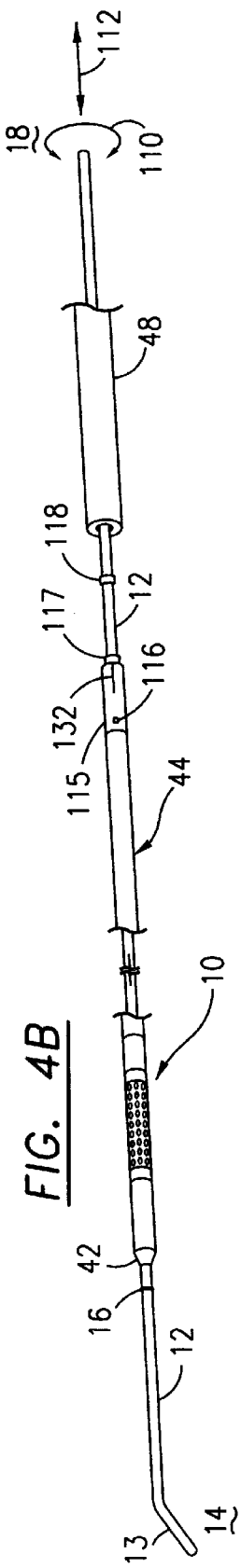
FIG. 4B
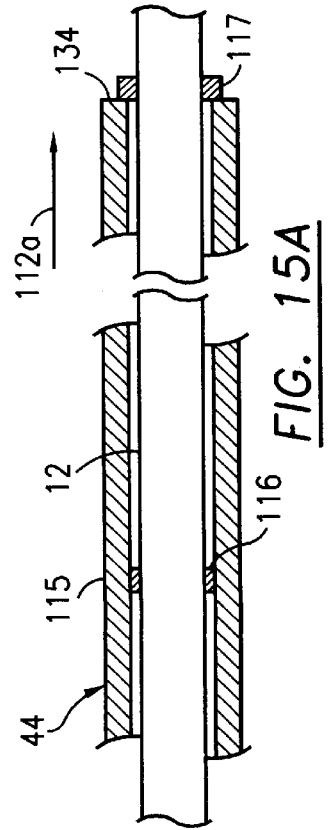
FIG. 15A
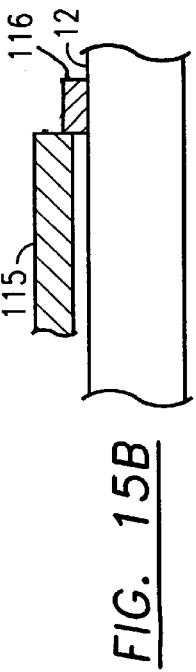
FIG. 15B
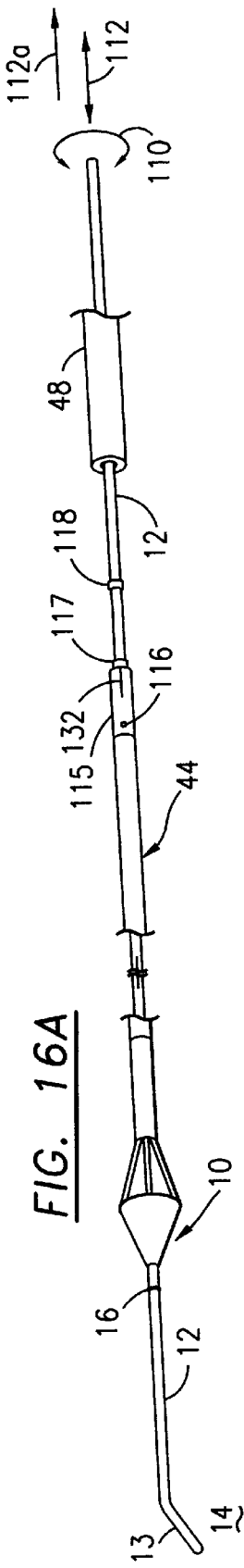
FIG. 16A
FIG. 17

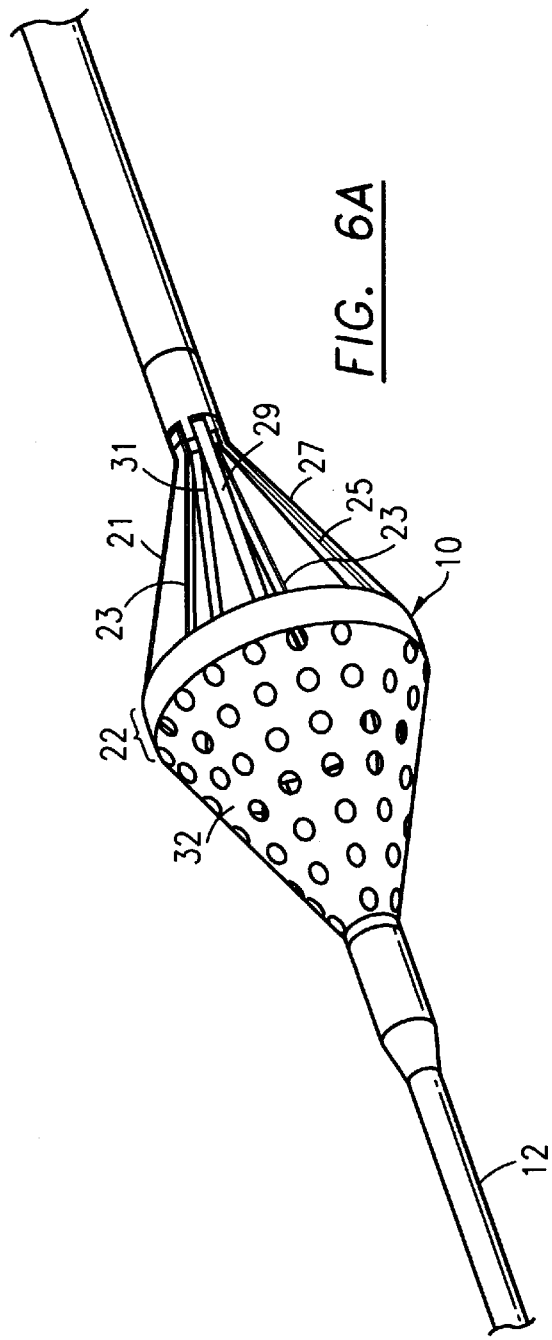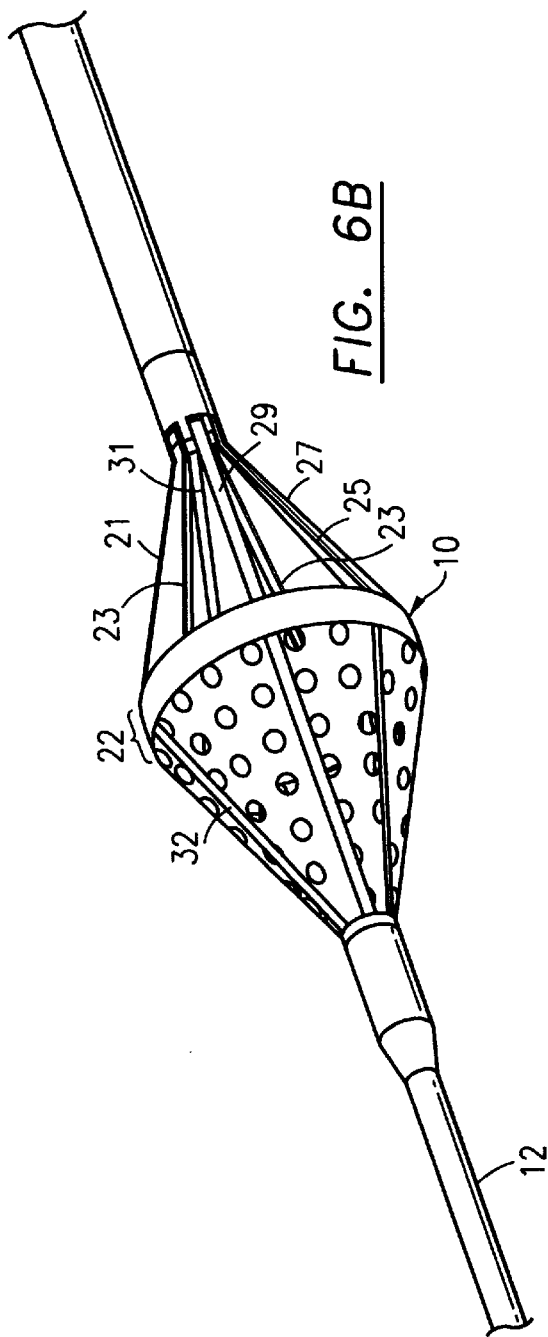

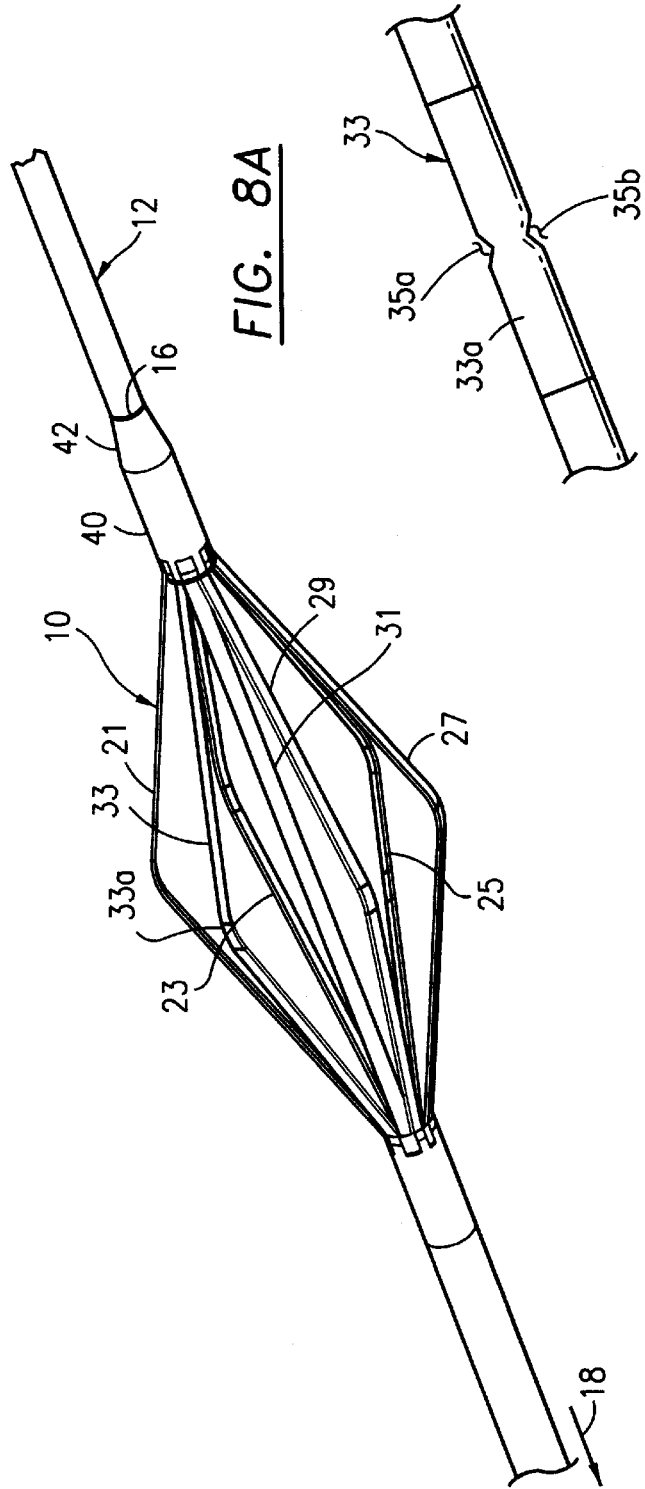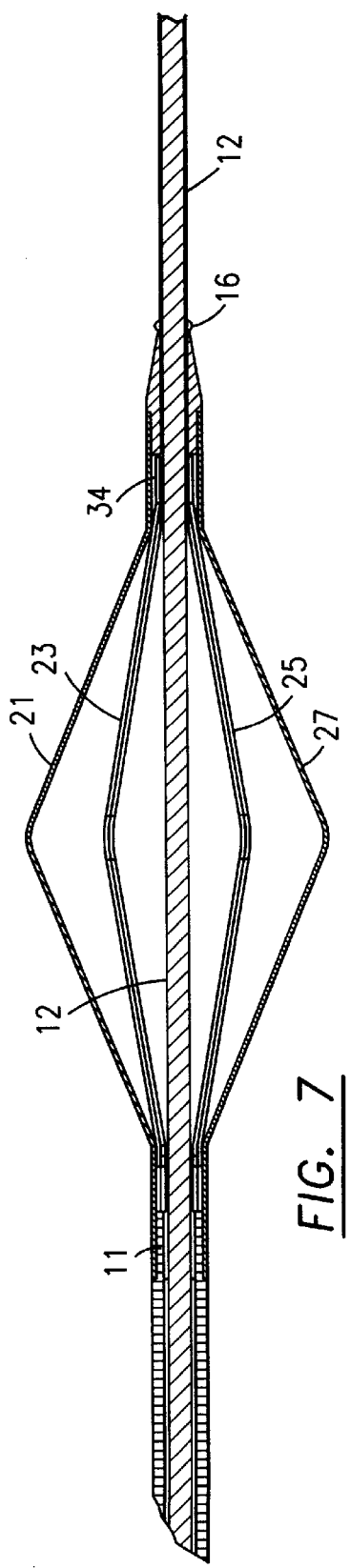

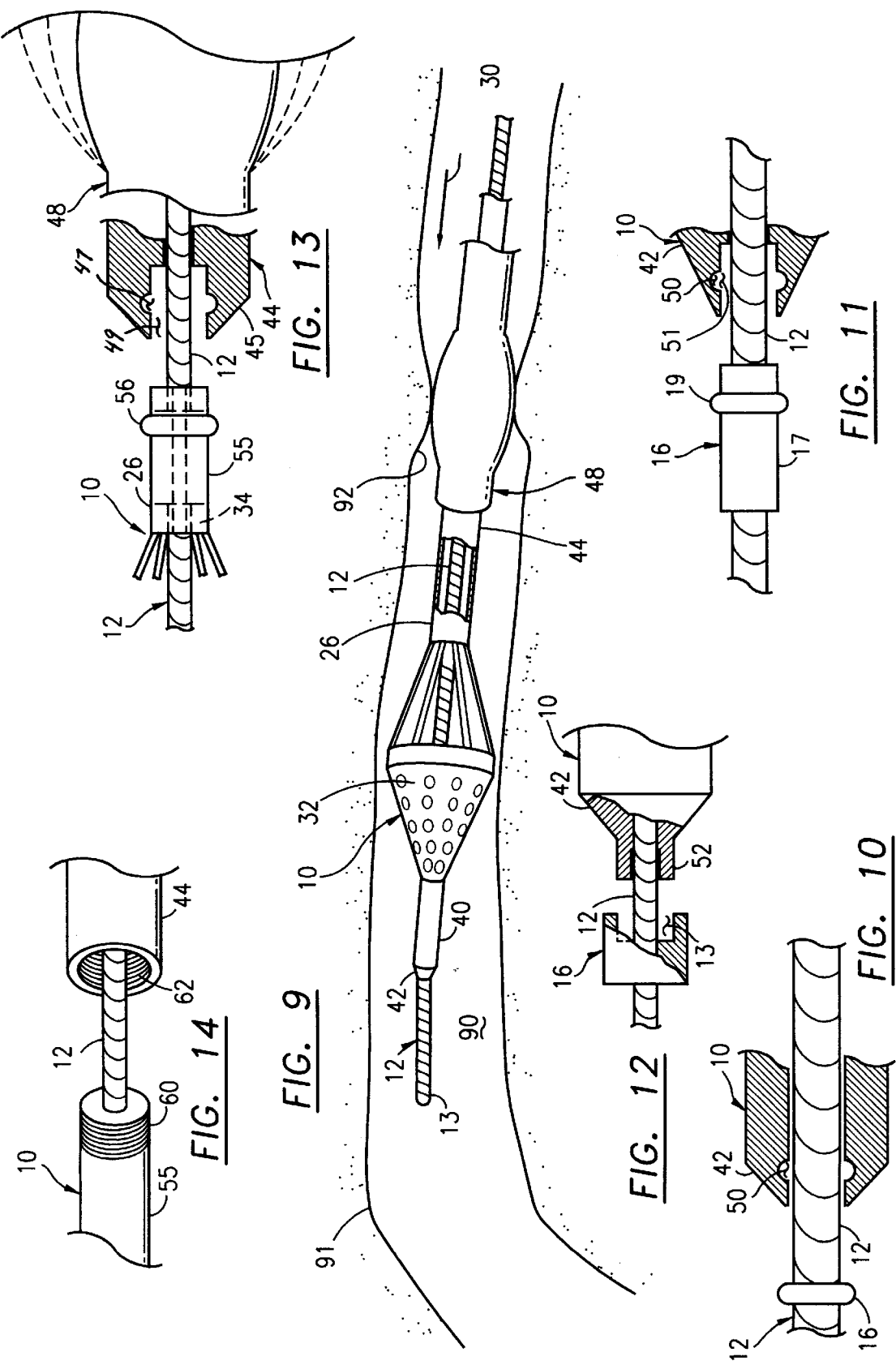

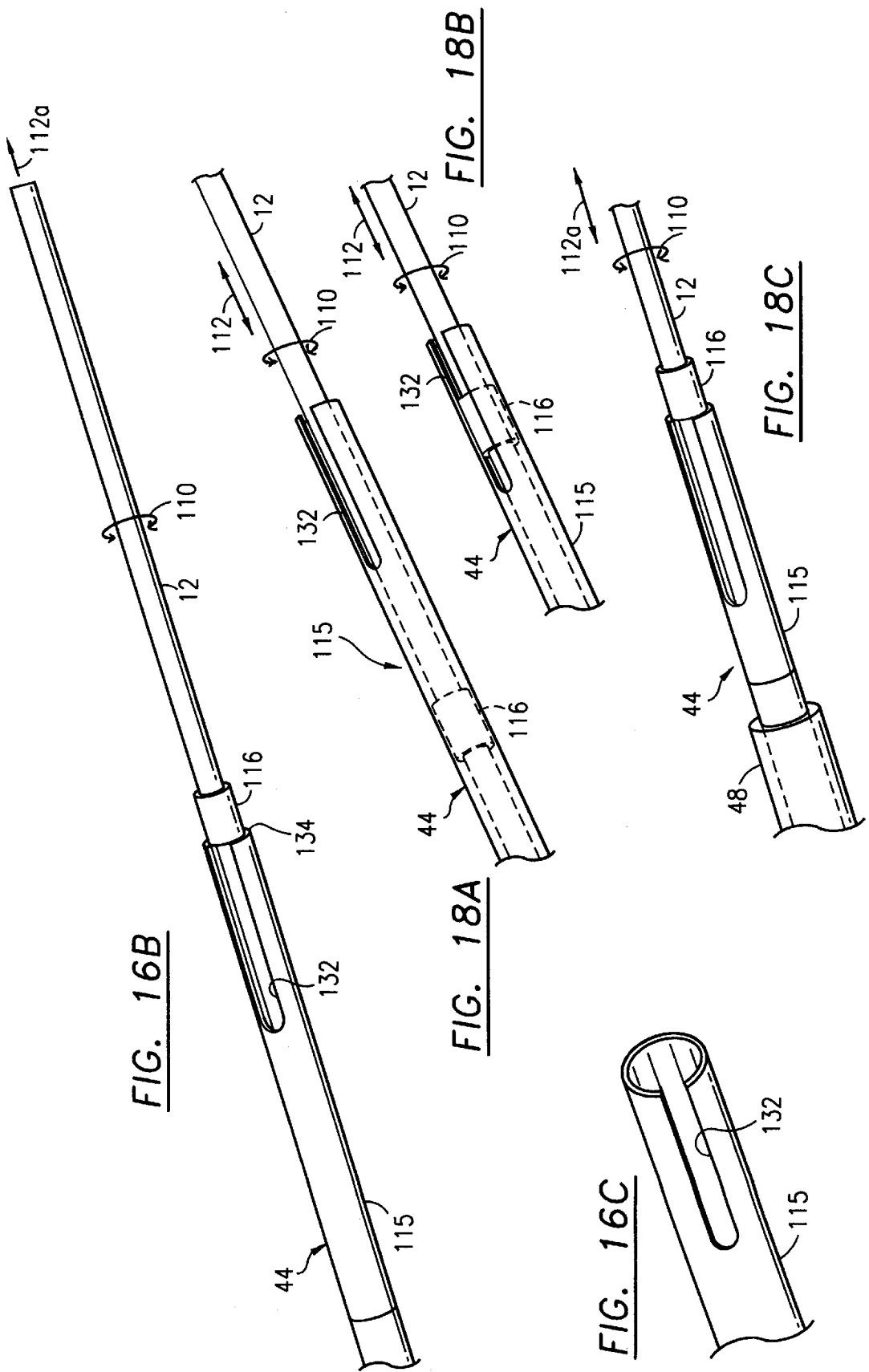

VASCULAR PROTECTION AND EMBOLIC MATERIAL RETRIEVER

This is a continuation-in-part of patent application Ser. No. 09/376,120 filed Aug. 17, 1999, now pending and provisional patent application Ser. No. 60/127,438 filed Apr. 1, 1999.

The present invention relates to a vascular protection and embolic material retriever utilized in conjunction with a guide wire utilized during catheterization of a patient.

BACKGROUND OF THE INVENTION

Vascular disease is the leading cause of death and disability in the world. An estimated 50 million people worldwide suffer from some form of coronary, cerebrovascular and/or peripheral vascular artery disease. Medical technology has advanced dramatically over the years, providing an overall decrease in the cost of care while improving a patient's quality of life. The primary advancement in the treatment of vascular disease has been the advent of catheter-based (or interventional) procedures, which have rapidly gained acceptance—growing from under 325,000 procedures in 1994 to over 1,000,000 in 1997—since they are less invasive and less costly compared to their open surgical counterparts.

Despite the rapid growth in catheter-based procedures, embolic events remain a major clinical problem. Embolic events are typically created by thrombus (blood clot) or plaque which break loose, enter the bloodstream, and become lodged in the artery resulting in the obstruction of blood flow.

Stroke is a form of cardiovascular disease that interrupts blood flow to the brain. A stroke occurs when the carotid artery leading to the brain becomes clogged (ischemic stroke) or bursts (hemorrhagic stroke), preventing oxygen-rich blood from reaching the brain. As a result, brain cells die. Once dead, they do not regenerate which is why damage from a stroke is frequently permanent. Stroke accounts for 10% to 12% of all deaths in industrialized countries. For example, in a population of one million, 1,600 people will have a stroke each year, of which only 55% will survive six months post-stroke, and a third of the survivors will have significant disability. Stroke ranks third in terms of leading causes of death in the United States, behind heart disease and cancer. Strokes cause an estimated 150,000 deaths each year and are the leading cause of long-term disability. Current treatment options include medical management (drug therapy), carotid endarterectomy, or stent-supported carotid angioplasty. Carotid endarterectomy has demonstrated a marked increase in its use during the past two years on the basis of pivotal studies demonstrating a reduction in stroke after carotid revascularization. It is well documented that carotid endarterectomies have a 3% to 6% complication rate, depending if the patient is asymptomatic or symptomatic. Embolization has represented an obstacle to widespread acceptance of stent-supported carotid angioplasty due to the brain's sensitivity to even small amounts of emboli, with clinically significant strokes occurring in the absence of angiographically definable branch vessel occlusions is to compete effectively against the endarterectomy, it must demonstrate equal complication rates. In particular, carotid angioplasty must not lead to an increase in embolization or stroke rates. Industry sources estimate roughly 100,000 carotid endarterectomies were performed in the Unites States alone in 1997. In the same year, approximately 90,000 procedures were performed internationally and these operations are increasing at a faster rate than the United States. The desire among patients to have—and cardiologists to perform—less invasive procedures is evident. Industry estimates indicate that the number of carotid angioplasty procedures in the United states will grow from roughly 3,000 in 1998 to approximately 36,000 procedures in 2002.

The use of an effective emboli capture device or filter could significantly reduce the risk of these often devastating complications, and could potentially become the standard of care—even in low risk cases.

During catheterization of a patient, a guide wire is directed through the patient's blood vessel to the site of interest. For example, the physician may wish to utilize a balloon catheter in order to enlarge a partially obstructed blood vessel at a certain location in the patient's vascular system. To do this, the physician utilizes a guide wire which is directed through the patient's vascular system to the particular site for balloon catheterization. Various medical devices are percutaneously inserted into the patient's blood vessel utilizing the guide wire. The balloon catheter, for example, is mounted at the distal end of an elongated tube. The guide wire is placed in the lumen of the balloon catheter tube such that the balloon catheter can be threaded over the guide wire, through the vascular system and placed at the site of interest by following the guide wire.

In order to enlarge a partially obstructed blood vessel, a physician may use various surgical techniques and biomedical devices or tools including balloon catheters, scrapers or other known medical devices. However, the utilization of these devices sometimes results in a release of an embolus (embolic material) which is an abnormal particle circulating in the blood. In order to reduce complications arising from these medical procedures, physicians sometime utilize filters disposed downstream of the site of interest. As used herein the term "downstream" refers to an item that is spaced a distance apart from a referenced item and in the direction of blood flow through the blood vessel.

U.S. Pat. No. 4,619,246 to Molgaard-Nielsen et al. discloses a collapsible filter basket. The basket includes a woven mesh but does not operate on a guide wire.

U.S. Pat. No. 4,723,549 to Wholey et al. discloses a filter which is expanded based upon inflation of a balloon acting as a donut mounted to expanding frame members of the filter disposed about the guide wire.

U.S. Pat. No. 5,053,008 to Bajaj discloses a filter which is expanded based upon inflation of a tubular balloon.

U.S. Pat. No. 5,108,419 to Reger et al. discloses a filter for capturing particles of plaque which includes a laterally (radially) collapsible bag with a plurality of longitudinally displaced filter cones therein. The bag has a draw string about its mouth which opens and closes the bag both laterally (to deploy or pull-up the conical filters) and longitudinally (to wrap the conical filters and the bag into a small-diameter shape). Each conical filter includes flexible tension supports which carry filter screens or mesh and which open and close based upon the respective longitudinal position of a generally static hub at the end of a guide wire running through the filter basket system. In another embodiment, a single conical filter is utilized with a filter stocking or collapsible bag thereabout. All the tension supports are flexible enough to wrap and twirl within the collapsible bag and wrap the conical filter(s) about the guide wire. Also, a draw string closes the collapsible bag in all embodiments. The flexible tension supports or radial ribs are resilient enough to provide force to spread the conical filter mesh across the lumen of the blood vessel.

U.S. Pat. No. 5,549,626 to Miller et al. discloses a filter deployed from the inside of a hollow tube by axial movement of an inner catheter. The filter is a mesh-like collapsible basket being made of radially expandable materials which can be compressed in the lumen of an outer catheter and radially expand when the basket extends beyond the distal end of the catheter.

U.S. Pat. No. 5,695,519 to Summers et al. discloses a wire, which controllably moves forward and aft, to open and close a generally conical filter by acting on the filter's mouth.

U.S. Pat. No. 5,810,874 to Lefebvre discloses a filter including strips that are radially opened by moving an inboard ring towards an outboard ring. The rings retain forward and aft ends of the strips. The filter can be detached from the guide wire.

U.S. Pat. No. 5,814,064 to Daniel et al. discloses one filter system which utilizes various types of inflatable ribs, tubes or struts and a second filter system wherein the filter material is deployed by longitudinal movement of a push-pull wire relative to a generally static distal end of a tube (see Daniel FIGS. 15–16B). In one embodiment, struts carry filter mesh and are forced radially outward by axial movement of a wire attached to the apex of the conical filter relative to a static tube end. In a collapsed position, the filter is disposed outboard of the static tube. In another embodiment, wire filter mesh has a conical memory shape such that when deployed outboard of a closed end cylinder, a conical filter is created by the memory shaped metallic filter. In another embodiment, only the open end of the conical filter has a memory shape. A further embodiment utilizes memory shaped filter mesh, a cinch wire and a push guide wire.

U.S. Pat. No. 5,911,734 to Tsugita et al. discloses a conical mesh filter with a proximal end strut structure connected to the distal end of a guide wire. Accordingly, the distal end of a guide wire is not downstream of the filter (see Tsugita FIGS. 2–8B). In another embodiment, the filter (conical or concave) is attached to radially outwardly biased struts. In a closed state, the biased struts are retained within a sheath. Upon axial movement of the guide wire relative to the sheath, the struts are moved beyond the sheath, they spring open to expand and deploy the filter. (See Tsugita FIGS. 10–11B). In a further embodiment, an egg beater filter is deployed. One embodiment of the egg beater filter utilizes a compressive spring which pulls fore and aft ends of expandable struts together, thereby radially expanding a filter basket with one side carrying filter mesh thereon. In other words, the filter is spring actuated. (Tsugita FIG. 15A). In another egg beater embodiment, pressure wires "spring" radially outward deploying conical cage wires which retain a mesh filter. (Tsugita FIG. 16). A scroll filter is also disclosed. A further embodiment discloses a filter with an expansion frame apparently made of memory shaped material. Tsugita FIG. 19 discloses a filter with a distally extending inner sheath having filter strut ends attached thereto and an outer sheath having the other filter strut ends attached thereto. To open the filter, the outer sheath is moved distally towards the inner sheath thereby causing the filter struts to buckle radially outward. The struts may be packed densely to form a filter or filter mesh material may be draped over the struts. In a different embodiment, an outer sleeve is longitudinally slitted. (Tsugita FIGS. 23, 23A). When the distal end of the slit outer sleeve is pulled proximally, the slitted region buckles radially outward to provide an egg beater filter. The expanded cage can be draped with filter mesh.

PCT Published Patent Application WO 96/01591 discloses a concave filter deployed by axially shortening the distance between the filter mouth and the filter apex (attached to a distal end of a guide wire). The filter mouth is sprung open by tethers fixed at one end to a static tube. A rod extends through the filter to its apex. The filter opens based upon the relative position of the filter apex on the rod (which extends beyond the apex to form the distal end of the guide wire) and the static tube.

OBJECTS OF THE INVENTION

It is an object of the present invention to provide a filter device for capturing embolic material in a blood vessel.

It is a further object of the present invention to provide a controllably deployed embolic material filter and retrieval device.

It is another object of the present invention to provide for a vascular protection and embolic material retriever retrieval device mounted on a guidewire which is movably disposed in a catheter sheath.

It is an additional object of the present invention to provide a retrieval device which can remove captured embolic material from the artery of a patient.

SUMMARY OF THE INVENTION

The vascular protection and embolic material retrieval device is used in connection with a guidewire and a catheter sheath during catheter based procedures. The device includes a discontinuous loop of memory sheath material having an open loop shape when the loop is not radially restrained in the catheter sheath. When the loop is disposed beyond the distal end of the catheter sheath, the loop is deployed and forms a discontinuous loop due to the memory characteristic of the loop material. The device includes a lead line having a proximal end attached to the guidewire and a distal end attached to the discontinuous loop. A substantially conical filter adapted to capture embolic material has an open conical end attached to the discontinuous loop and a conical end point attached to the guidewire. When the loop is disposed outboard of the catheter sheath, the filter unfurls forming a conical filter trap for embolic material. In order to collapse the filter, the guidewire is pulled such that the lead line, loop and conical filter moves inboard towards the sheath's distal end and the filter collapses about any embolic material trap therein.

BRIEF DESCRIPTION OF THE DRAWINGS

Further objects and advantages of the present invention are found in the detailed description of the preferred embodiments when taken in conjunction with the accompanying drawings in which:

FIG. 1 diagrammatically illustrates a cross-sectional view of the deployed filter device for capturing embolic material in a blood vessel;

FIG. 2 diagrammatically illustrates a collar at either the fore end or the aft end of the expandable frame and frame struts;

FIG. 3 diagrammatically illustrates the bent region of the frame strut and the partial wrap of non-perforated material around that bent region;

FIG. 4A diagrammatically illustrates the radially closed compact form of the expandable frame extending over the guide wire;

FIG. 4B diagrammatically illustrates the expandable frame filter in a radially closed compact form, on a guide wire and linked to an actuation tube and proximal lock with a catheter deployed at a proximal end of the filter, frame and actuator system;

FIG. 5 diagrammatically illustrates a cross-section of the radially closed compact form filter and illustrates the perforated filter material furled within the closed compact form of the expandable frame (the material being furled prior to deployment);

FIGS. 6A and 6B diagrammatically illustrate perspective views of the deployed expandable frame with the filter material on the outside of the frame struts and the filter material on the inside of the frame struts, respectively;

FIGS. 7 and 8A diagrammatically illustrate a cross-sectional view of the expandable frame and frame struts without the filter material and a perspective view of the deployed frame struts, respectively;

FIG. 8B diagrammatically illustrates a plane view of the transitional bent region of the frame struts;

FIG. 9 diagrammatically illustrates the expandable frame and deployed filter material mounted on the guide wire and utilized in connection with a balloon catheter;

FIGS. 10, 11 and 12 diagrammatically illustrate various stops and latch mechanisms operable in connection with the filter device;

FIG. 13 diagrammatically illustrates a further lock and latch system in order to operate the expandable frame;

FIG. 14 diagrammatically illustrates a threaded lock between the expandable frame filter and the actuation tube;

FIGS. 15A and 15B diagrammatically illustrate actuator tube latches at the proximal end of the guard wire, blood filter frame and actuator tube;

FIG. 16A diagrammatically illustrates a deployed filter and the position of the "light touch" latch at the proximal end of the actuator tube (and the introduction of a catheter tube over the filter system and actuator tube);

FIG. 16B diagrammatically illustrates a detailed view of a guide wire and the light touch, filter deployed latch system;

FIG. 16C diagrammatically illustrates the proximal end of the actuator tube latch;

FIG. 17 diagrammatically illustrates the catheter tube being introduced over the actuator tube;

FIGS. 18A, 18B and 18C diagrammatically illustrate the positional relationship of the catch or latch ring on the latch tube of the actuator for the fully radially closed position (FIG. 4A), a partially deployed position and a radially fully opened position (FIG. 1);

DETAILED DESCRIPTION OF THE PREFERRED EMBODIMENTS

Figure 6C:
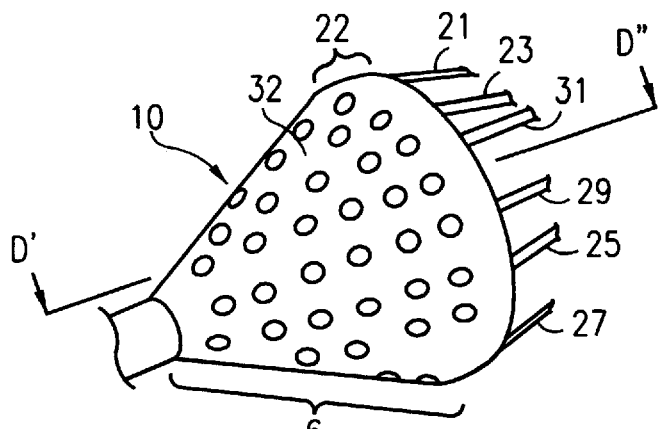
FIG. 6C diagrammatically illustrates a perspective view of a deployed expandable frame with perforated filter material without the delineation of the bent region for the frame members.

The present invention relates to a vascular protection and embolic material retriever.

FIG. 1 diagrammatically illustrates a cross-sectional view of filter device 10 generally freely traveling on guide wire 12. Filter 10 can rotate and move longitudinally over guide wire 12 except for longitudinal movement beyond stop 16 towards distal end region 14 of the wire 12. More importantly, the guide wire 12 moves freely through filter device 10. Guide wire 12 has a proximal end shown by arrow 18. Stop 16 is mounted near the distal end of the guide wire.

Filter device 10 includes an expandable frame 20 formed of a plurality of frame struts. Frame struts 21, 23, 25 and 27 are identified in the cross-sectional view of FIG. 1. In a preferred embodiment, each of the frame struts 21, 23, 25 and 27 have a bent region 22. In a preferred embodiment, bent region 22 is preformed and is centrally located generally midway between the fore region 24 and the aft region 26 of expandable frame 20 on frame struts 21, 23, 25 and 27.

In the radially deployed state, expandable frame 20 forms a pair of facing, frustoconical frame structures 6, 28. The mouth of frustoconical frame structure 6 in the illustrated embodiment is upstream of fore end 24. As implied earlier, the term "upstream" refers to a position opposite the direction of blood flow 30 shown by the single headed arrow in FIG. 1.

Filter material 32 (typically PET material having perforations (generally 80 holes, 400 microns each)), is attached to frame struts 21, 23, 25 and 27 forming frustoconical frame structure 6. In FIG. 1, filter material 32 is attached to the outside of frame struts 21, 23, 25 and 27 (FIG. 1 representing a cross-sectional view of the deployed filter device 10). The aft end of filter material 32 (proximally disposed with respect to fore end 24 of filter device 10), has a non-perforated or drilled material region about bend transition region 22. This is better shown in FIG. 3 which is discussed below. The non-perforated region enhances a sealing against the lumen of the blood vessel.

One important functional feature of the present invention involves the free movement of guide wire 12 within and through filter device 10. This freedom of movement, both radially and longitudinally along the length of the guide wire is accomplished by fore and aft collars 11, 34 of the filter 10.

FIG. 2 diagrammatically illustrates aft collar 34 movably disposed on guide wire 12. Similar 14 numerals designate similar items throughout the drawings.

FIG. 3 diagrammatically illustrates frame strut 21 having bent transition region 22. Filter material 32 has a non-perforated material portion in bent region 22. Non-filtering region 22 generally restricts blood flow therethrough. This general flow resistant region 22 of material 32 operates differently compared to blood flow region of filter 32. Blood flow is generally shown by arrow 30 in FIG. 1. The material utilized for filter 32 in the blood flow through region 33 (FIG. 3) is drilled or perforated. Other filters are known to persons of ordinary skill in the art. Generally, blood molecules flow through filter flow region of material 32 at region 33 but embolic material is captured by the filter thereat. These embolic materials are sometimes created by balloon catheterization, stenting or other surgical techniques acting on a surgical site upstream of filter device 10. This is illustrated and generally described later in connection with FIG. 9.

FIG. 4A diagrammatically illustrates filter device 10 in a radially compact form prior to deployment of the expandable frame. Guide wire 12 includes a coiled tapered end 13 at distal region 14. In some situations, the end 13 of guide wire 12 may be curved to enable the physician to better guide and place the guide wire in the desired vessel of the patient. See the curved blood vessel in FIG. 9. Filter device 10 includes a generally cylindrical fore end piece 40 and a tapered fore end segment 42. At aft end segment 26, filter device 10 includes an actuation sleeve or tube 44 which extends in direction 18 to the proximal end of the guide wire (not shown). FIG. 4A also shows a further surgical instrument 48 which is utilized by the physician to repair, replace, mount a stent or utilize another biomedical structure or tool at an upstream location with respect filter device 10. Instrument 48 is commonly called a catheter.

In general, the operation of filter device 10 is as follows. The physician deploys the guide wire 12 in the blood vessel of the patient at or near the surgical site of interest. Filter device 10 is customarily carried by guide wire 12 through the vascular system. Hence, rotational and longitudinal freedom of movement of filter device 10 (integrated with actuation sleeve 44) with respect to guide wire 12 is important. The filter device 10 and actuation sleeve 44 runs with guide wire 12 as an integrated system or unit. See FIG. 4B.

Either before or after the physician threads or places balloon catheter or other surgical device 48 over the actuation sleeve 44 and hence over guide wire 12, the physician may radially deploy the expandable frame 10 in the following manner. The fore end 42 of expandable filter device 10 contacts stop 16 on guide wire 12. This position is shown diagrammatically in FIG. 1. Before such contact, the physician may twist (torque) the guide wire through the vascular system. The guide wire freely moves rotatably and longitudinally through the filter device 10 (except for movement beyond stop 16).

At that point in time or shortly thereafter at stop 16, the physician continues to exert a forward force on filter actuation tube or sleeve 44 in the longitudinal or axial direction with respect to guide wire 12 (e.g. pulling the guide wire while pushing actuation tube 44) thereby causing compression of filter 10 and sleeve 44 and frame struts 21, 23,25, 27, 28, 29 and 31 and causing the struts to radially expand to the position shown in FIG. 1. Radial expansion is limited by either the interior size of the blood vessel or the mechanical limits of the non-filter material about bent region 22. In the pre-deployed state and in a preferred embodiment, filter material 32 is furled within radial compact structure.

Figure 19:
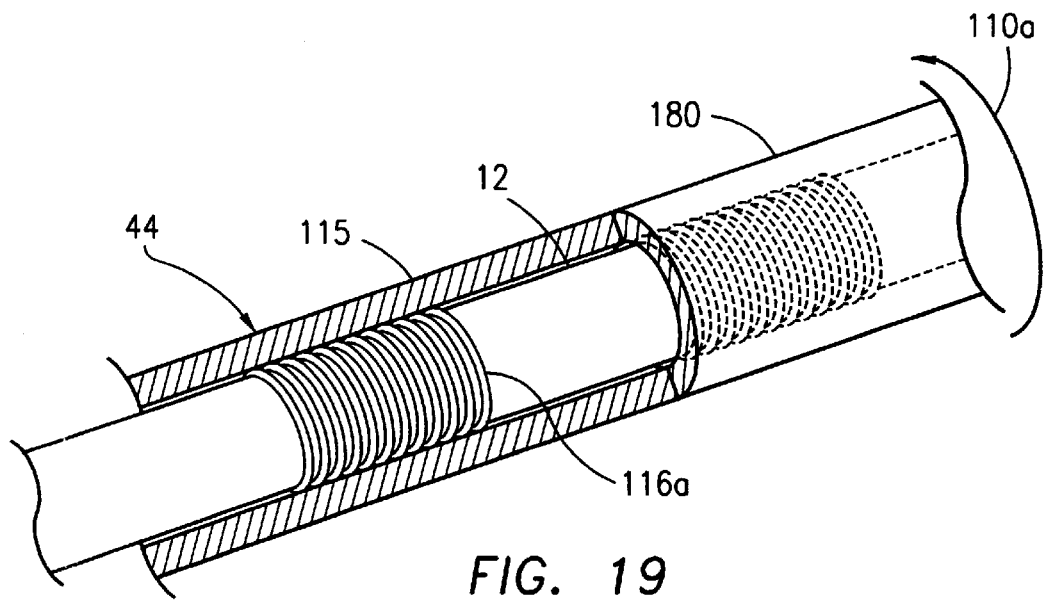
FIG. 19 diagrammatically illustrates a thread control to manually deploy the filter, the thread control established between the threaded catch on the guide wire and the threads at the proximal end of the actuator cylinder.

The operation of actuation sleeve 44 and actuator piece 115 (shown in FIG. 4B) is discussed later in detail in connection with FIGS. 15A, 15B, 16A, 17, 16B, 16C, 18A, 18B, 18C. Alternative actuator and latch systems are shown in FIG. 19.

FIG. 5 diagrammatically shows filter material 32 furled or disposed in the interior of the closed radially compact form of expandable frame 20. FIG. 5 shows expandable 20 with frame struts 21, 23, 25, 27, 29 and 31.

After deployment and formation of frustoconical frame structures 6, 28, the physician (a) threads device 48 (e.g. catheter 48) over guide wire 12 and actuation sleeve 44 and (b) activates the balloon catheter or other biomedical device 48 which is upstream, relative to blood flow, of the deployed expandable frame 10. After the surgical procedure with biomedical device 48, expandable frame 10 is collapsed by the physician or other medical technician by longitudinally pulling actuation sleeve 44 in a proximal direction relative to the guide wire 12. The collapse of expandable frame 10 is achieved by (a) temporary retention of the fore end 40,42 of expandable frame 10 or (b) closing spring action of the frame or (c) both retention and closing spring action. Temporary retention of the frame is shown diagrammatically with certain lock or latch structures in FIGS. 10–12 which are discussed later. Upon collapse, filter 32 captures and entraps embolic material and this embolic material is withdrawn from the blood vessel of the patient by proximal withdrawal of actuation sleeve 44 and expandable frame filter device 10 over guide wire 12.

FIGS. 6A and 6B diagrammatically illustrate filter material 32 on the outside of frame struts 21, 23, 25, 27, 29 and 31 and on the inside of those frame struts, respectively.

FIG. 6C diagrammatically illustrates filter device 10 in a radially deployed state. Filter material 32 has a filtering region substantially covering frustoconical frame structure 6. However, there is no clear demarcation (other than the absence of holes and passage ways) between filter material 32 and peripheral bend region 22 which is a non-filter region.

Figure 6D:
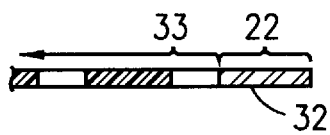
FIG. 6D diagrammatically illustrates the non-perforated material disposed around the bent transition region of the frame and the beginning of the perforated filter area.

FIG. 6D diagrammatically illustrates a plane view showing non-filter region 22 and the filter region 33 from the perspective of a portion of section line D'–D" in FIG. 6C.

Figure 6E:
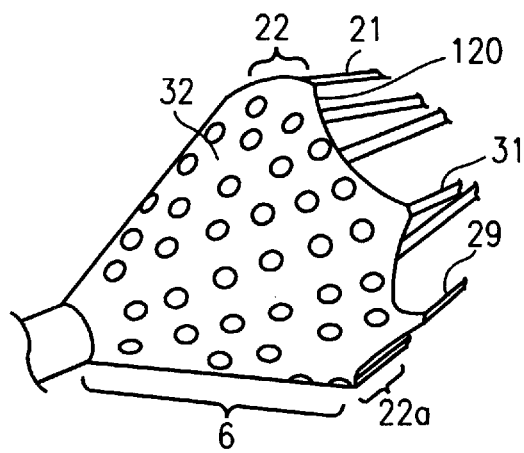
FIGS. 6E, 6F and 6G diagrammatically illustrate a deployed expandable frame in a fully open state with filter material having a scalloped edge, a partially closed state, and a further closed state (the fully closed state diagrammatically illustrated in FIGS. 4A and 5)
Figure 6F:
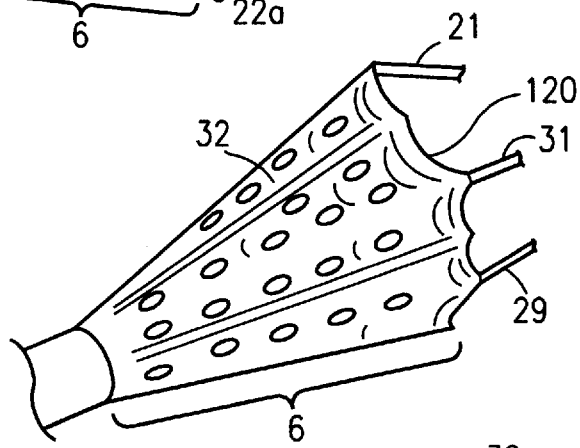
Figure 6G:
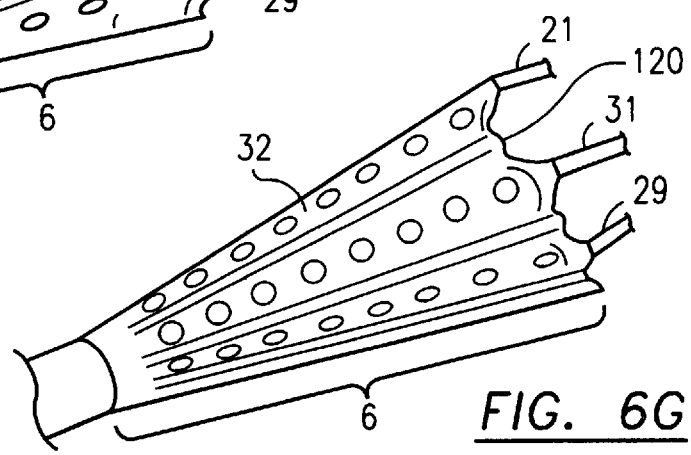

FIGS. 6E, 6F and 6G diagrammatically show a scalloped edge in the non-filter bend region 22–22a. FIGS. 6F and 6G diagrammatically illustrate various collapsed states or positions for frustoconical frame structure 6. The utilization of scallop or concave edge regions spanning adjacent struts (see concave or scallop edge region 120 between the adjacent struts 21, 31), enable the filter material 32 to furl and gather either beneath the frame strut (FIG. 6B) or about the frame strut (FIG. 6A) in order to achieve radial containment upon collapse and prior to withdrawal similar to that illustrated in FIG. 5. FIG. 6F diagrammatically illustrates that filter material 32 gathers and furls upon partial radial collapse of frustoconical frame structure 6 due to the concave or scallop nature of the material between the complementary frame struts, that is complementary to adjacent struts 21, 31. FIG. 6G shows that concave edge 120 promotes gathering of filter material 32 between the complementary frame struts associated with struts 21, 31. As used herein, the term "complementary frame struts" refers to struts attached to adjacent struts 21, 31 and struts which form the frustoconical frame structure 6 upon which is disposed filter material 32.

FIGS. 6E, 6F and 6G diagrammatically illustrates that filter device 10 can be constructed to collapse and gather the filter material 32 as an umbrella.

FIGS. 7 and 8A diagrammatically illustrate a cross sectional view and a perspective view of the deployed frame struts 21, 23,25,27, 29 and 31. FIG. 8A diagrammatically shows an additional frame strut 33. Accordingly, filter device 10 can include a plurality of frame struts if necessary.

FIG. 8A also diagrammatically shows the bend transition region 33a for frame strut 33. In a preferred embodiment the frame struts are preformed (pre-shaped) and bent at transition region 33a such that upon axial or longitudinal compression between stop 16 and the proximal region of guide 12, the frame struts expand at a predetermined common point. Preferably, the common point is centrally located on the struts. Preferably, the struts also have a "memory" which biases the struts to a closed position. See FIG. 4A. FIG. 8B shows a further enhancement wherein the struts are notched at 35a, 35b to facilitate a consistent and predictable bent region 33a. Notches or cutouts 35a, 35b are preferably disposed at the midpoint of complementary frame strut members.

FIG. 9 diagrammatically illustrates the deployed filter device 10 disposed in a blood vessel 90 of a patient. Guide wire 12 has been generally placed near the site of interest and slightly distally beyond the site of interest. The site of interest is partial blockage or occlusion 92 in blood vessel 90 of the patient. It is desirable to have guide wire 12 move, with respect to filter 10, freely both radially and longitudinally except filter 10 will not move distally beyond stop 16 on guide wire 12. This freedom of movement (two degrees of freedom) permits the guide wire to move through the blood vessel 90 and particularly about blood vessel bend 91. In operation, the physician deploys expandable frame 10 downstream of medical device or catheter 48 relative to blood flow 30. Device 48 is placed and runs over the outside of actuation tube or sleeve 44 which is operatively associated with aft end region 26 of filter device 10. By longitudinal compression (a force directed distally by the physician via actuation sleeve 44), filter device 10 radially expands thereby deploying filter material 32. Filter material 32 has a filter size (perforations or hole diameter 400 microns) adequate to capture embolic material which may be dislodged by the medical procedure at site 92 upstream of filter 10. Biomedical device 48 in FIG. 9 is a general illustration of a balloon catheter. Actuator sleeve 44 and the collapsed filter device 10 easily passes within a 0.05 inch lumen of catheter 48.

FIGS. 10–12 diagrammatically illustrate various stop configurations and latches to enable (a) deployment of filter material 32 and (b) collapse and retrieval of the filter device 10 from surgical site 92. FIG. 10 illustrates stop 16 as a ring attached to guide wire 12. The fore end piece 42 of filter device 10 includes a channel 50 which is complementary or slightly smaller than guide ring-stop 16. When guide ring 16 is placed in channel 50 of fore piece 42, filter device 10 is latched onto and temporarily locked to guide wire 12. This latch or lock permits both radial deployment of filter 32 (see FIGS. 1 and 9) and also permits the closure of the filter by proximally moving actuation sleeve in a direction away from ring stop 16. This movement is relative to the guide wire.

FIG. 11 shows a cylindrical stop 16 having a generally cylindrical body 17 and a protruding ring 19. Fore end piece 42 of filter device 10 includes a complementary cavity 50, complementary to the shape of ring like protrusion 19 and a larger fore end cavity 51 which is complementary to the aft end shape of cylindrical fixed stop collar 17. The operation is substantially similar as that discussed above in connection with FIG. 10.

FIG. 12 diagrammatically illustrates another configuration of stop and latch 16 which includes a radially inboard aft channel 13. The fore end 42 of filter device 10 includes a protruding end piece 52 that is complementary to aft end channel 13 of fixed lock collar stop 16. Again, the physician distally moves filter device 10 until fore end key piece 52 locks into channel 13 of collar stop 16. Further distal movement of actuation sleeve 44 over guide wire 12 (which is static or "not moving") causes radial deployment of the expandable frame struts of filter device 10. To withdraw the filter device 10, the physician proximally pulls actuation sleeve 44 thereby collapsing the frame struts, collapsing the frustoconical frame structure 6 (FIG. 1), collapsing filter material 32 and capturing any embolic material which did not pass through filter material 32. Typically, the collapse is assisted by the closing spring action of the frame struts. The lock and latch system consisting of channel 13 and key latch 52 is strong enough to result in the collapse of the frame strut and the filter mesh. Upon further proximal movement of actuation sleeve 44 and after full collapse of the expandable frame 10, the locking force of channel 13 and lock latch 52 is overcome by the pulling force of the physician, fore end latch piece 52 exits locking channel 13 and the filter device 10 is withdrawn from the blood vessel 90.

FIG. 13 diagrammatically illustrates an aft end locking latch system. Aft end region 26 of filter device 10 includes an aft cylindrical end 55 with a ring collar 56. Actuation sleeve 44 includes a fore end piece 45 with a locking complementary channel 47 and a larger mating channel 49. Mating channel 49 passes over the aft end of aft member 55 of filter device 10. Locking channel 47 is complementary to the shape of collar protrusion 56 thereby enabling the actuation sleeve 44 to latch onto the ring collar 56. In this manner, the actuation sleeve 44 can be attached and detached from the filter device 10. If detached, the balloon catheter or other biomedical device 48 travels directly over the guide wire rather than over actuation sleeve 44. The forces necessary to latch and unlatch the fore end 40, 42 of filter device 10 must be commensurate or balanced with respect to the locking and latching features on the aft end 55, 56 of filter device 10.

In addition, FIG. 14 shows that aft end piece 55 of filter 10 can be threaded and carry a set of threads 60 which are complementary to thread set 62 on actuation sleeve 44. By locking and latching the fore end of filter 10 via one or more of the systems shown in FIGS. 10–12, the actuation sleeve 44 can be threaded onto aft piece 55 of filter device 10. Of course, the male and female thread features of the system shown in FIG. 14 can be reversed such that aft 55 defines female threads and actuation sleeve 44 carries male threads.

As discussed earlier in connection with FIG. 4B, filter 10 operates based upon longitudinal movement of actuator sleeve or tube 44. Longitudinal movement 112 is noted with respect to filter device 10, actuator 44 with respect to guide wire 12.

It is important that the physician be notified tactilely (via touch) and visually that filter device 10 is approaching distal end stop 16 which is permanently affixed to guide wire 12. In order to provide such notification, FIG. 4B utilizes three temporary stops or latch points 116, 117, 118. However, it should be noted that only a single temporary stop or latch point 116 may be utilized in connection with the present invention.

FIG. 15A diagrammatically illustrates a partial, cross-sectional detailed view of actuator piece 115 which is part of actuator sleeve 44. Preferably, actuator piece 115 is cylindrical and is made with a more rigid material as compared with actuator sleeve 114. Most of the materials utilized in connection with filter device 10 and actuator sleeve 44 are stainless steel. Filter struts are preferably Ni Ti. Filter material 32 is preferably drilled (with a laser) and filter material 32 and non-filter region 22 is preferably made of PET. Actuator piece 115 is preferably a tube of NiTi. Other materials may be utilized as known to persons of ordinary skill in the art.

In the illustrated embodiment of FIGS. 4B and 15A, three stops (temporary stops) or latch points 116, 117 and 118 are utilized. Temporary stop 118 provides an initial indication to the physician that filter device 10 is soon approaching distal end stop 16. Intermediate temporary 117 is a tactile and a visual notice of the close approach of nose piece 42 to stop 16.

FIG. 15A diagrammatically shows that temporary stop 117 has a slightly larger outside diameter as compared with the inside diameter of actuator piece 115. As described later, actuator piece 115 has a longitudinal slot 132 therethrough which permits the aft region of actuator piece 115 to move radially. Accordingly, the physician is permitted to hold or withdraw actuator piece 115 in the direction shown by arrow 112a in FIG. 15A thereby causing actuator piece 115 to radially expand and "jump over" temporary stop 117.

FIG. 15B diagrammatically shows the slight radial overlap between temporary stop 116 and actuator piece 115. All latch points 116, 117, 118 have a similar radial relationship with respect to the interior or inner diameter of actuator piece 115. Accordingly, every time aft edge 134 of actuator piece 115 passes over temporary stop or latch points 116, 117, 118, the physician is tactilely notified and can visually confirm the position of filter device 10 in relation to distal end stop 16. By providing consistent, repeatable and reportable distance relationships between stops 116, 117, 118 and the radial deployment and/or longitudinal position of the filter basket and distal end stop 16, the physician or the operator can easily control the distance and radial expansion (and contraction) of filter device 10 in relation to end stop 16.

More importantly, distal end stop 116 is utilized to expand filter device 10 as shown in FIG. 16A.

FIG. 16A diagrammatically illustrates a radially expanded filter device 10 which is achieved by the physician longitudinally pushing actuator sleeve 44 such that actuator piece 115 is distally located or longitudinally inboard with respect to temporary stop or latch point 116. Even with filter 10 radially deployed as shown in FIG. 16A, the physician can easily rotate guide wire 12 as shown by double headed arrow 110 and also move the entire guide wire and temporarily latched and deployed filter 10 in the direction shown by double headed arrow 112a. FIG. 16A also shows that biomedical device or catheter 48 can be fed over temporary stops 116, 117, 118, actuator piece 115, actuator sleeve 44 and lead to a point near the aft end of deployed filter device 10.

FIG. 17 shows catheter 48 extending over actuator sleeve 44. Guide wire 12 protrudes proximally out of the rear end of catheter biomedical instrument 48.

In order to radially collapse filter device 10, the physician pulls actuator piece 115 in the direction shown by arrow 112a in FIG. 16A thereby overcoming the temporary latch 116, partially radially expanding actuator piece 115 and longitudinally withdrawing actuator sleeve 44 with respect to guide wire 12. As discussed earlier, the frame struts form filter device 10 preferably have a memory which biases the frame struts to a closed position. This feature enhances closure of the filter device 10.

FIG. 16B diagrammatically illustrates actuator piece 115 disposed at the proximal end of actuator sleeve 44. Actuator piece 115 includes a longitudinal slot 132. The proximal end 134 of actuator piece 115 is temporarily caught on latch point 116. It should be noted that actuator piece 115 may have a plurality of slots or may be made of a material which easily radially expands in order to overcome temporarily latch points 116, 117, 118. Also, rather than having square peripheral edges, the latch point edges may be rounded. Other latch point shapes may be utilized.

FIG. 16C provides a detailed view of slot 132 and actuator piece 115.

FIGS. 18A, 18B and 18C diagrammatically illustrate the various positional aspects of actuator piece 115 in relation to critical temporary latch point 116. In FIG. 18A, latch point 116 is at an inboard position relative to actuator piece 115. The physician can easily rotate guide wire 12 in the direction shown by double headed arrow 110 and may also longitudinally move guide wire 12 in relation to filter device 10 as shown by double headed arrow 112. In FIG. 18B, latch point 116 is disposed beneath slot 132. This position provides several advantages. First, the physician may tactilely and visually see temporary latch 116 as it travels within slot 132. Preferably, upon visual or tactile confirmation that sleeve 115 as been placed such that latch 116 is adjacent slot 132, the filter device 10 is radially deployed at various positionally related states of radial deployment. In other words, when actuator piece 115 is positioned such that temporary latch 116 is disposed at or near the inboard or distal end of slot 132, the frustoconical frame 6 begins to radially open filter material 32 (assuming that the actuator is moving distally with respect to a stationary guide wire). At the slot mid-point (FIG. 18B), frustoconical frame 6 is approximately 50% radially open. When actuator piece 115 is completely disposed inboard or at a distal position relative to temporary latch point 116 (FIG. 18C), frustoconical frame structure 6 is fully radially deployed.

Figure 20:
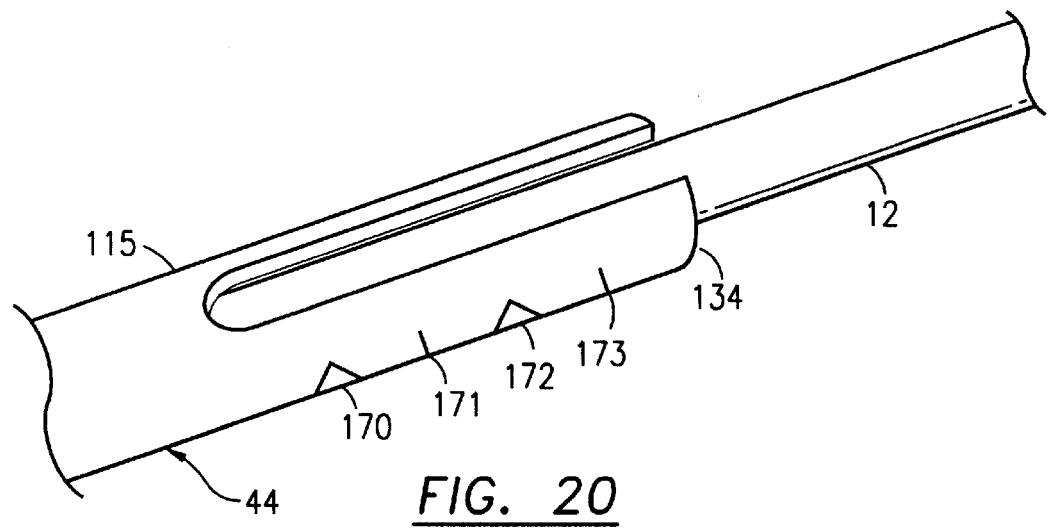
FIG. 20 diagrammatically illustrates a latch cylinder with indicia marking the radial deployment of the filter at the distal end of the system.

FIG. 20 diagrammatical illustrates actuator piece 115 having various indicia or markings 170, 171, 172, 173 which show and provide a visual indication to the physician that the filter device 10 begins its opening sequence (indicia 170), is 25% open (indicia 171), is 50% open (indicia 172), is 75% open (point 173) and is fully open when proximal end 134 of actuator piece 115 is located at an inboard or distal position relative to temporary latch point 116.

Other types of temporary latches or stops can be provided at the proximal end of actuator sleeve 44. For example, FIG. 19 diagrammatically illustrates that critical latch 116a has a male thread defined thereon and a proximal region 180 of actuator piece 115 has a female thread thereon. When the male thread of latch 116a mates with the female thread on proximal region 180 of actuator piece 115, filter device 10 begins to radially deploy. Upon rotation in a direction, for example direction 110a, the physician by rotating actuator piece 115 radially expands filter device 10 by further threading threaded member section 180 of actuator piece 115 over threaded latch 116a.

In some situations, embolic material trapped in the filter may limit full radial closure of the filter (to a state similar to FIG. 4A). If the embolic material carrying filter is radially large (relative to the fully closed position FIG. 4A), the physician, subsequent to the withdrawal of the catheter, (a) places a guide wire extender on the proximal end of the guide wire; (b) longitudinally withdraws the actuator tube and the "full" filter basket while leaving the distal end of the guide wire at the point of interest; (c) withdraws the filter basket proximally beyond the guide wire extender; (d) unmounts the extender from the guide wire proper; and (e) proceeds with other surgical techniques (which may include the use of a new filter basket and/or a catheter or stent). This procedure is particularly useful when a stent is placed in the patient's blood vessel.

FIGS. 21–25 diagrammatically illustrate the embolic material filter and retrieval device. The conical filter 220 may be similar to filter 32 in FIGS. 6A or 6C. The retrieval device may be used in connection with balloon 48 in FIG. 9. Also guide wire 204 in FIG. 21 may be extended as explained earlier.

Figure 21:
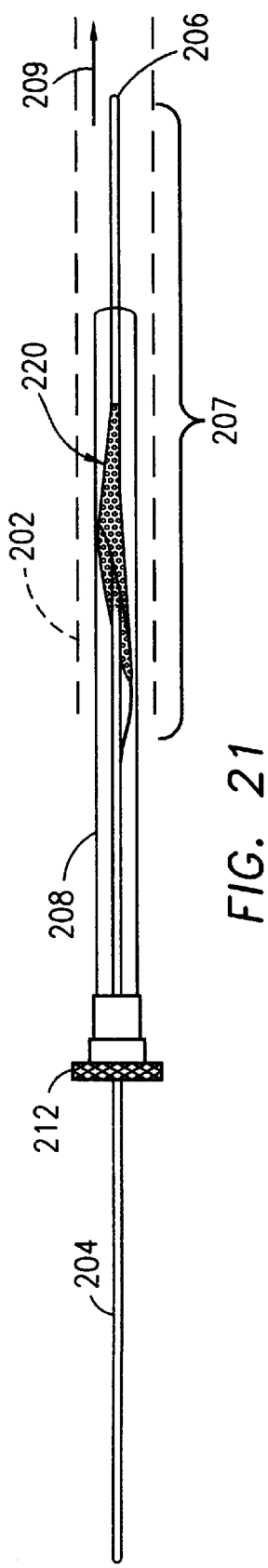
FIG. 21 diagrammatically illustrates a vascular protection and embolic material retriever wherein the retrieval device is mounted on a guidewire and the retrieval device is disposed inboard a catheter sheath.

The embolic filter and retrieval device in FIG. 21 prevents embolization during interventional and surgical coronary and vascular procedures without compromising blood flow. The device is low profile as to prevent the dislodging of plaque or thrombus when crossing the lesion. The device is based on a guidewire 204 (FIG. 21) which is used to guide the operator to the obstructed vessel 202. The guidewire has a soft floppy tip 206 to prevent vessel dissection or damage. The guidewire 204 is made of a material to enable it to be visible under x-ray. At the distal end portion 207 of the guidewire, a wire loop 224 is attached to act as frame for the filter 222. The guidewire 204 is attached to the loop 224 via led 226 then continues on through the center of the loop. The conical end point 300 of filter 222 is attached to guide wire 204. The loop 224 is made of shape memory alloy. The wire is trained so that it assumes a substantially round loop design and size in an unrestrained free state. A filter material 222 is attached to the loop 224 by various known methods and is distally attached to the guidewire at cone end shape 300. The filter material 222 allows blood to flow freely through, but traps debris, which may be potentially dangerous to the patient. The device 220 is introduced in the patient inside a tube catheter (sheath 208) to completely encase the distal filter 220 as shown in FIG. 21. The sheath 208 is anchored on the proximal portion to the guidewire with a Toughy-Borst locking mechanism (screw down locking device), to prevent the sheath 208 from sliding on the guidewire 204. Once the filter 220 is properly positioned in the vessel 202, the protective sheath 208 is removed which allows the filter 220 to open conical shape filter material 222 and take shape. See FIG. 22. The filter opens to the internal diameter of the vessel 202 and traps any debris which make detach during the catheter based procedure. The device may also be used as a retriever of devices that may have malfunctioned or stones.

Toughy-Borst locking mechanisms are described in U.S. Pat. No. 5,951,458; U.S. Pat. No. 5,855,546 and U.S. Pat. No. 5,484,416.

Catheter based procedures are typically performed under fluoroscopy (x-ray) to help guide the user through the vasculature. The device 220 is introduced in the patient as an ordinary guidewire 204. The guidewire 204 has a soft floppy tip 206 to prevent vessel dissection or damage. The guidewire 204 is made of a material to enable it to be visible under x-ray. The guidewire 204 with protective sheath 208 is introduced into vessel 202. The operator navigates the wire through the vessel 202 with the help of x-ray. Once the distal portion 207 of the guidewire 204 and the filter-loop 220 completely pass the obstruction in the blood vessel, the sheath 208 is removed or drawn proximally towards the user by loosening the Toughy-Borst lock down mechanism 212, and then withdrawing the catheter 208.

The blood flow in direction 209 will open up the filter material 222, just as a parachute opens when exposed to wind. The loop 224 has a gap in one embodiment (see FIG. 24) and hence is discontinuous to allow the loop 224 and filter 222 to open enough to make contact with the vessel inner wall 202. The gap allow the loop 224 to open to various sizes. Once the operator removes the protective sleeve 202, a device (not shown) may be loaded on the guidewire. Normally a catheter with a balloon attached at the distal end is used. See FIG. 9. The balloon catheter (typically used during angioplasty) has a hollow opening to allow the catheter to be placed over the guidewire. The catheter is threaded over the guidewire 204. Once the operator reaches the obstruction with the balloon, the balloon is inflated to push the plaque or thrombus to the sides and allow blood to flow unrestricted. See FIG. 9. The balloon is then deflated and removed. The operator can then remove the guidewire or insert a catheter with a stent mounted on the balloon. The catheter again is threaded over the guidewire. Once the balloon is inside the plaque, the balloon is inflated to deploy and open the stent. The stent acts as a scaffold to prevent the vessel from future closure. The balloon is deflated and withdrawn.

Once the balloon catheter is removed, the operator is now ready to remove the guidewire 204. A sheath 208 is threaded over the guidewire 204 to the filter location. The sheath 208 has a larger opening at the distal tip 210 to allow the filter 220 to slowly collapse and enter the catheter. See FIG. 23. The catheter is moved forward to allow the loop portion and the filter to completely enter the distal portion of the catheter. The loop 224 is made of a material that will allow it to completely collapse. The filter 222 is a material, which is soft enough with minimal wall thickness to fold into the catheter. When the filter 220 enters the catheter, any debris captured is located at the distal portion of the filter, which prevents any debris from escaping.

The sheath 208 is, in one embodiment, constructed of thin walled plastic in order to add only minimally to the guidewire/filter diameter. The sheath 208 can be thin walled enough to allow for substantial flexibility, since the sheath is supported by the guidewire/filter. At the proximal end of the sheath a luer-lock is attached with a locking device to tighten the sheath over the guidewire/filter.

The guidewire/filter is made of a proximal flexible metal wire 204 which then becomes tapered distally 207 with a spring wire wound around the tapered core wire to give the wire flexibility, steerability and shapeability. The guidewire distal portion 207 has a soft tip 206 so as to be atraumatic.

The loop 224 is attached to the distal portion 207 via lead 226 of the guidewire. The loop 224 is of a smaller diameter than the guidewire 204. The loop 224 contains a gap in one embodiment to allow the loop to enlarge. The loop is made from a shape memory alloy which exhibits superelasticity. The wire 224 is trained so that it assumes a predetermined shape and size in an unrestrained free state. From this trained free state configuration (FIG. 22), the loop can expand to a large loop and contract to flat state without permanent deformation from the trained intermediate state. Compare FIGS. 21, 22 and 23. This range of movement allows the loop 224 to be easily deployed and withdrawn into the sheath.

The filter material 222 is thin walled and porous to allow blood to flow unimpeded. The filter 222 is rolled in a cone shape with the wide portion attached to the loop 224 in various methods and the closed narrow portion attached to the guidewire. The guidewire extends continuously through the center of the loop and the distal center of the cone shaped filter.

Figure 22:
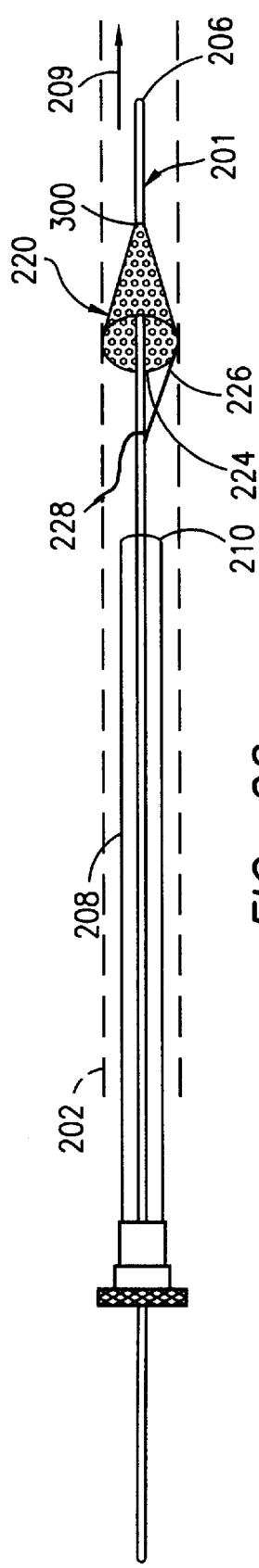
FIG. 22 diagrammatically illustrates a deployed embolic material retriever (deployed outboard of the distal end of the catheter sheath)
Figure 23:
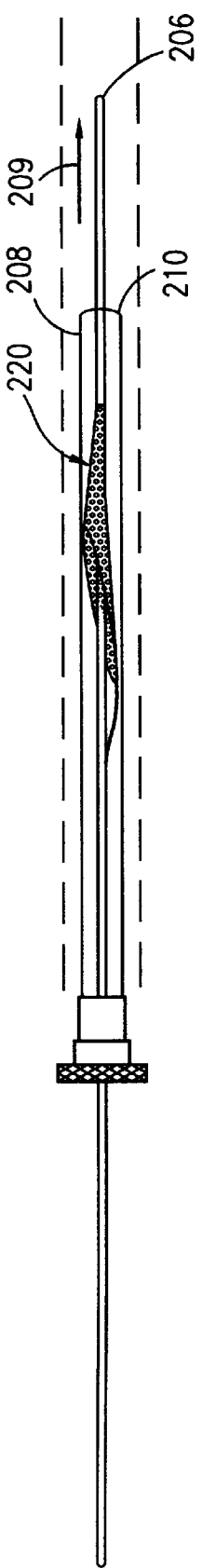
FIG. 23 diagrammatically illustrates the retrieval device being hold inboard of the catheter sheath.
Figure 24:
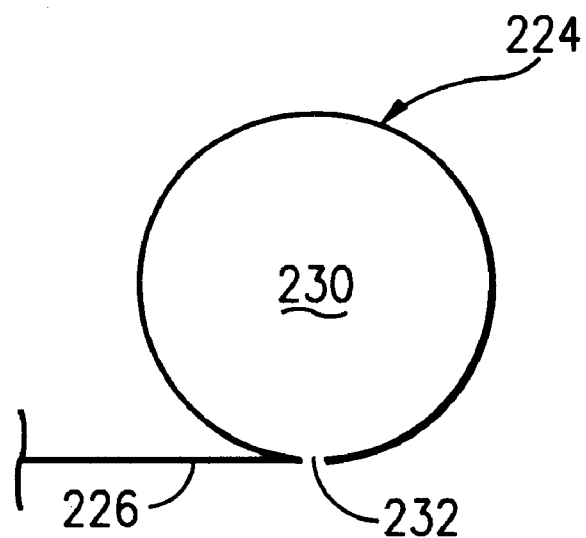
FIG. 24 diagrammatically illustrates one embodiment of the discontinuous loop for the embolic material retrieval device.
Figure 25:
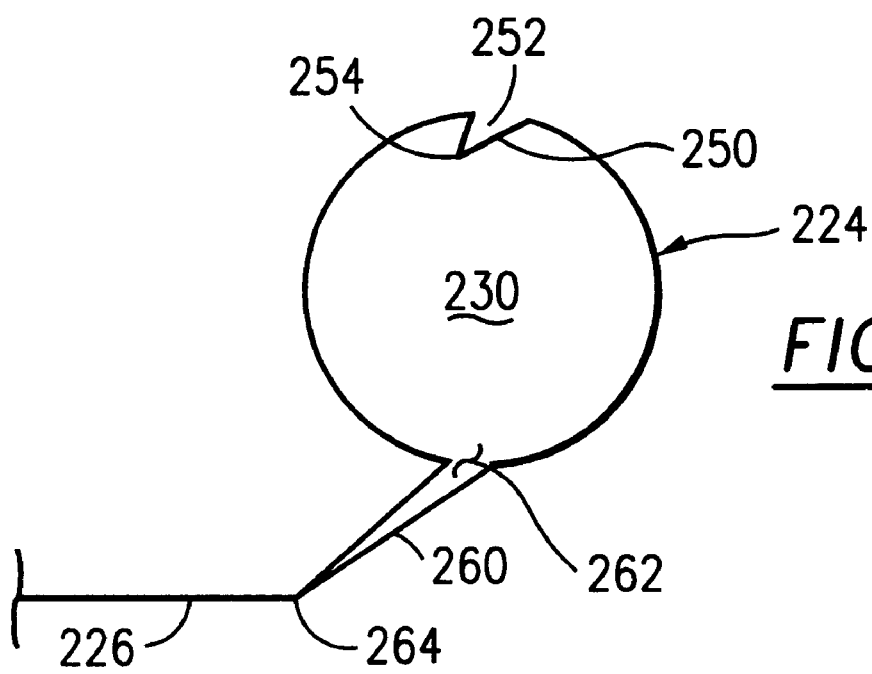
FIG. 25 diagrammatically illustrates another embodiment of the discontinuous loop.

FIGS. 24 and 25 show discontinuous loops 224. In FIG. 24, loop 224 has a gap 232. Lead wire 226 is attached to loop 224. The other end 228 of lead 226 is attached to guidewire 204 as shown in FIG. 22. Gap 232 creates a discontinuity in the substantially circular shape of loop 224. This discontinuity enables loop 224 to vary the size of space 230.

In FIG. 25, the discontinuity is an inboard protruding element 250 having, in this embodiment, an inboard protrusion 254 directed inboard towards loop space 230. FIG. 25 shows an open ended triangle element 250 with an open side 252 outboard of loop space 230. Multiple inboard elements 250 may be utilized. FIG. 25 also shows a second discontinuous element 260 protruding outboard of space 230 and interposed between lead 226 and loop 224. This outboard protruding triangular element 260 has an open end 262. Open end 262 may operate in a similar manner to gap 232 in FIG. 24, that is, to facilitate the size of loop space 230 in blood vessel 202.

Loop 224 may be made of NITINOL or memory shaped stainless steel. Filter 222 may be mesh or a sheet of urethane drilled with holes (typically laser drilled holes). A complete collapse of filter device 220 may not be necessary to retrieve the device. A partial collapse wherein the open end of conical filter 222 is near or at distal end 210 of sheath 208 may be acceptable.

The claims appended hereto are meant to cover modifications and changes within the scope and spirit of the present invention.

What is claimed is:

1. An embolic material retrieval device adapted for use with a guide wire adapted to extend through and beyond a distal end of a catheter sheath and during catheter based procedures comprising:
    a discontinuous loop of memory shape material having an open loop shape when not radially restrained, said discontinuous loop defining a circumferentially closed, generally circular shape with an inboard protruding discontinuity adapted to enable generally radial collapse of said loop, said inboard protruding discontinuity forming at least one, open ended triangular segment;
    a lead line having a proximal end adapted to be attached to said guide wire and a distal end attached to said discontinuous loop;
    a substantially conical filter adapted to capture embolic material, an open conical end of said filter attached to said discontinuous loop and a conical end point adapted to be attached to said guide wire;
    whereby said discontinuous loop and the attached filter are adapted to be collapsed when proximally disposed in said catheter sheath and inboard the sheath's distal end and said discontinuous loop and the attached filter are adapted to be deployed in a substantially conical shape when distally disposed outboard said sheath's distal end.

2. A device as claimed in claim 1 wherein said filter is one of a mesh filter and a sheet filter defining a plurality of holes through said sheet.

3. A device as claimed in claim 2 wherein said loop includes an outboard protruding discontinuity forming an open ended triangular segment with an open end disposed inboard said loop and an apex attached to said lead line.

4. A device as claimed in claim 1 wherein said discontinuous loop defines a circumferential gap at said open triangle end in the open loop state.

5. A device as claimed in claim 4 wherein said gap is substantially normal to said lead line.

6. A device as claimed in claim 1 wherein said discontinuous loop is substantially normal to said lead line when not radially restrained.

7. A device as claimed in claim 1 wherein both said lead line and said discontinuous loop are made of memory shape material.

8. A device as claimed in claim 1 wherein said loop includes an outboard protruding discontinuity forming an open ended triangular segment with an open end disposed inboard said loop and an apex attached to said lead line.

9. An embolic material retrieval device adapted for use with a guide wire adapted to extend through and beyond a distal end of a catheter sheath and during catheter based procedures comprising:
    a singular strand of memory shape material forming a circumferentially discontinuous loop with a small arcuate gap about its circumference, said discontinuous loop also forming a substantially larger axially open loop shape with said small arcuate gap when not radially restrained, said small arcuate gap remaining open when said discontinuous loop is not radially restrained;
    a lead line having a proximal end adapted to be attached to said guide wire and a distal end attached to said discontinuous loop;
    a substantially conical filter adapted to capture embolic material, an open conical end of said filter attached to said discontinuous loop and a conical end point adapted to be attached to said guide wire;
    whereby said discontinuous loop and the attached filter are adapted to be collapsed when proximally disposed in said catheter sheath and inboard the sheath's distal end and said discontinuous loop and the attached filter are adapted to be deployed in a substantially conical shape when distally disposed outboard said sheath's distal end.

10. A device as claimed in claim 9 wherein said gap is substantially normal to said lead line.

11. A device as claimed in claim 10 wherein both said lead line and said discontinuous loop are made of memory shape material.

12. A device as claimed in claim 11 wherein said loop includes an outboard protruding discontinuity forming an open ended triangular segment with an open end disposed inboard said loop and an apex attached to said lead line.

13. A device as claimed in claim 7 wherein said loop includes an outboard protruding discontinuity forming an open ended triangular segment with an open end disposed inboard said loop and an apex attached to said lead line.

14. An embolic material retrieval device adapted for use with a guide wire adapted to extend through and beyond a distal end of a catheter sheath and during catheter based procedures comprising:
    a discontinuous loop of memory shape material having an open loop shape when not radially restrained, said loop having an outboard protruding discontinuity forming an open ended triangular segment with an open end disposed inboard said loop, said triangular segment also defining an apex;
    a lead line having a proximal end adapted to be attached to said guide wire and a distal end attached to said discontinuous loop via said apex of said triangular segment;
    a substantially conical filter adapted to capture embolic material, an open conical end of said filter attached to said discontinuous loop and a conical end point adapted to be attached to said guide wire;
    whereby said discontinuous loop and the attached filter are adapted to be collapsed when proximally disposed in said catheter sheath and inboard the sheath's distal end and said discontinuous loop and the attached filter are adapted to be deployed in a substantially conical shape when distally disposed outboard said sheath's distal end.

15. An embolic material retrieval device adapted for use with a catheter sheath and during catheter based procedures, said catheter sheath having a distal end, comprising:

a guide wire adapted to extend through and beyond said distal end of said sheath a discontinuous loop of memory shape material having an open loop shape when not radially restrained;

a lead line having a proximal end attached to said guide wire and a distal end attached to said discontinuous loop;

a substantially conical filter adapted to capture embolic material, an open conical end of said filter attached to said discontinuous loop and a conical end point attached to said guide wire;

whereby said discontinuous loop and the attached filter are collapsed when proximally disposed in said catheter sheath and inboard the sheath's distal end and said discontinuous loop and the attached filter are deployed in a substantially conical shape when distally disposed outboard said sheath's distal end; and wherein said discontinuous loop, when not radially restrained within said catheter sheath, defines a closed, generally circular shape and further defines an inboard protruding discontinuity enabling generally radial collapse of said loop upon insertion of said lead line, loop and filter into said distal end of said catheter sheath.

16. A device as claimed in claim 15 wherein said filter is one of a mesh filter and a sheet filter defining a plurality of holes through said sheet.

17. A device as claimed in claim 15 wherein said discontinuous loop defines a gap in the open loop state.

18. A device as claimed in claim 15 wherein both said lead line and said discontinuous loop are made of memory shape material.

19. A device as claimed in claim 15 wherein said inboard protruding discontinuity forms at least one, open ended triangular segment.

20. A device as claimed in claim 15 wherein said loop includes an outboard protruding discontinuity forming an open ended triangular segment with an open end disposed inboard said loop and an apex attached to said lead line.

21. An embolic material retrieval device adapted for use with a catheter sheath and during catheter based procedures, said catherter sheath having a distal end, comprising:

a guide wire adapted to extend through and beyond a distal end of a catheter sheath;

a singular strand of memory shape material forming a circumferentially discontinuous loop with a small arcuate gap about its circumference, said discontinuous loop also forming a substantially larger axially open loop shape with said small arcuate gap when not radially restrained, said small arcuate gap remaining open when said discontinuous loop is not radially restrained;

a lead line having a proximal end adapted to be attached to said guide wire and a distal end attached to said discontinuous loop;

a substantially conical filter adapted to capture embolic material, an open conical end of said filter attached to said discontinuous loop and a conical end point adapted to be attached to said guide wire;

whereby said discontinuous loop and the attached filter are adapted to be collapsed when proximally disposed in said catheter sheath and inboard the sheath's distal end and said discontinuous loop and the attached filter are adapted to be deployed in a substantially conical shape when distally disposed outboard said sheath's distal end.

22. A device as claimed in claim 21 wherein said loop includes an outboard protruding discontinuity forming an open ended triangular segment with an open end disposed inboard said loop and an apex attached to said lead line.

* * * * *